United States Patent
Kuo et al.

(10) Patent No.: US 7,479,113 B2
(45) Date of Patent: Jan. 20, 2009

(54) METHOD AND DEVICE FOR AUTOMATICALLY DETERMINING HEART VALVE DAMAGE

(75) Inventors: Tsung-Ter Kuo, Tai Chung Hsien (TW);
Mao-Shun Su, I Lan Hsien (TW);
Yu-Kon Chou, Hsintien (TW);
Ming-Kaan Liang, Hsin Chu (TW)

(73) Assignee: Industrial Technology Research Institute, Hsinchu Hsien (TW)

( * ) Notice: Subject to any disclaimer, the term of this patent is extended or adjusted under 35 U.S.C. 154(b) by 655 days.

(21) Appl. No.: 11/060,437

(22) Filed: Feb. 18, 2005

(65) Prior Publication Data

US 2006/0089560 A1    Apr. 27, 2006

(30) Foreign Application Priority Data

Oct. 22, 2004    (TW)    ............................ 93132247 A

(51) Int. Cl.
*A61B 5/02*    (2006.01)
(52) U.S. Cl. ........................................................ 600/528
(58) Field of Classification Search .................. 600/528
See application file for complete search history.

(56) References Cited

U.S. PATENT DOCUMENTS 4,619,268 A    10/1986    Uphold et al.
2003/0072457 A1    4/2003    Grasfield et al.

FOREIGN PATENT DOCUMENTS

WO    WO 2004/032741 A1  *  4/2004

* cited by examiner

*Primary Examiner*—Mark W Bockelman
*Assistant Examiner*—Eric D Bertram
(74) *Attorney, Agent, or Firm*—Rabin & Berdo, P.C.

(57) ABSTRACT

A method and device for automatically detecting heart valve damage for four heart valves are proposed. The automatic determination method makes use of three or more heart tone microphones to simultaneously record heart tones of a patient's heart, and then separates the heart tones into four heart tone signals of the aortic valve, the pulmonary valve, the tricuspid valve and the mitral valve of the heart based on the timing characteristics and related techniques. Next, these four heart tone signals are digitally processed into sampling signals. Subsequently, the convolution method is used to process the sampling signals for producing system transfer functions. Finally, the system transfer functions and the reference database are compared to verify and determine damage for the four heart valves. The automatic determination method can judge heart valve damage to enhance the quality and convenience of medical treatment.

3 Claims, 3 Drawing Sheets

METHOD AND DEVICE FOR AUTOMATICALLY DETERMINING HEART VALVE DAMAGE

BACKGROUND OF THE INVENTION

1. Field of the Invention

The present invention relates to a method for automatically determining heart valve damage and a device for performing the same and, more particularly, to a method and device for automatically determining and judging heart valve damage.

2. Description of Related Art

The heart is an important organ of the human body, and operates all the time. A heart with a small problem badly affects the health of the human body. A clear description of the heart is difficult because it is a very complicated organ. Therefore, the measurement of heart tones is still the most common method used by doctors in clinical diagnosis of the heart status.

The heart pulsation results in flow and circulation of the blood. There will be changes in tissue form and fluid mechanics during the pulsation period. Sounds emitted due to these changes can be heard by using a stethoscope. These sounds are called heart tones. Heart murmurs are caused by turbulent flow of the blood. They can be divided into the systolic period, the diastolic period and the sustaining period according to the occurrence time. They can also be divided into the aortic valve, the pulmonary valve, the tricuspid valve and the mitral valve according to the diagnosis positions. A valve is like a door for controlling the blood to flow in a certain direction. For instance, the aortic valve is located between the left ventricle and the main artery, and controls the blood supply of the whole human body. For a patient with a narrow aortic valve, there will be a pressure difference between the left ventricle and the main artery when the heart contracts. The narrower the aortic valve, the larger the pressure difference. A doctor can thus find the heart murmur of the systolic period.

The heart tones can be divided into a first heart tone, a second heart tone, a third tone and a fourth heart tone. The first heart tone occurs at the initial stage when the heart contracts, and includes two components caused by the closure of the mitral valve and the tricuspid valve. The second heart tone occurs at the last phase when the heart contracts, and also includes two components caused by the aortic valve and the pulmonary valve. The third heart tone occurs at the initial stage when the heart expands. The fourth heart tone occurs at the last phase when the heart expands. The first and second heart tones are sounds generated when the valves close and are thus easy to observe. The third and fourth heart tones are less apparent and thus difficult to observe. Abnormal sounds, sounds other than these four heart tones, are viewed as heart murmurs. These heart murmurs represent symptoms of heart diseases including valve stenosis, valve regurgitation, valve cracks, or other defects in structure.

Therefore, the heart tone diagnosis is an important tool for a doctor to determine the heart status. A series of stethoscopes have been developed to help doctors determine the heart status. For example, the US. Pat. App. No. 20030072457 discloses an electronic stethoscope, which provides three operation modes. The first operation mode only filters out the physiologic sounds of the heart. The second operation mode only filters out the physiologic sounds of the lung. The third operation mode enhances the observation of abnormal heart tones through comparison of normal and abnormal heart tones at different amplification ratios. This electronic stethoscope, however, does not automatically help the doctors analyze the damage of heart valves.

U.S. Pat. No. 4,619,268 discloses an esophageal stethoscope and vital signs monitoring system, which can discriminate the heartbeat sounds and breath sounds of the lung and then calculate out the heartbeat rate and the breath rate of the lung for monitoring the vital signs of a patient. This esophageal stethoscope and vital signs monitoring system, however, also does not automatically help the doctors analyze the damage of heart valves.

The above conventional stethoscopes can't automatically help the doctors to analyze the damage of heart valves. The determination of heart tones still depends on the subjective judgment of a doctor, and is thus subject to environmental and artificial influences such as the doctor's age, hearing sensitivity, and the training degree of the auscultation skill. This problem may cause erroneous judgment of the damage of the heart valves.

SUMMARY OF THE INVENTION

An object of the present invention is to provide an automatic determination method and device of the damage of heart valves to enhance the quality and convenience of medical treatment.

To achieve the above object, the present invention provides an automatic determination method of the damage of heart valves. This method comprises the following steps. First, a reference database, which stores relationship data between accumulated clinical damages of heart valves and heart tones for assisting in analysis and judgment, is installed in advance. Three or more heart tone microphones are then used to pick up and record heart tones. Next, the heart tones are separated into four heart tone signals of the aortic valve, the pulmonary valve, the tricuspid valve and the mitral valve of the heart based on the timing characteristics and related techniques. Subsequently, these separated heart tone signals are digitally processed into sampling signals. Convolution is then performed to operate the sampling signals to produce system transfer functions. Finally, the system transfer functions of the heart valves are separately compared with the built-in reference database to verify and determine the damage of the four heart valves.

The present invention also provides an automatic determination method of the damage of heart valves. This device comprises a reference database, heart tone microphones, a heart tones separating unit, a heart tone signal digital processing unit, a convolution unit, a comparison unit and a display. The reference database is used for storing relationship data between accumulated clinic damages of heart valves and heart tones. The heart tone microphones are used for recording heart tones. The heart tones separating unit is connected with the heart tone microphones and used to separate the heart tones into four heart tone signals of the aortic valve, the pulmonary valve, the tricuspid valve and the mitral valve of the heart based on the timing characteristics and related techniques. The heart tone signal digital processing unit is connected with the heart tones separating unit and used to process the separated heart tone signals of the heart valves into sampling signals. The convolution unit is connected with the heart tone signal digital processing unit and used to process the sampling signals for producing system transfer function through the convolution method. The comparison unit is connected with the convolution unit and the reference database and used to compare separately the system transfer functions of the four heart valves to know the damages of the four heart valves. The display is connected with the comparison unit and used to display the damage of the heart valves.

BRIEF DESCRIPTION OF THE DRAWINGS

The various objects and advantages of the present invention will be more readily understood from the following detailed description when read in conjunction with the appended drawing, in which.

DETAILED DESCRIPTION OF THE PREFERRED EMBODIMENTS

Figure 1:
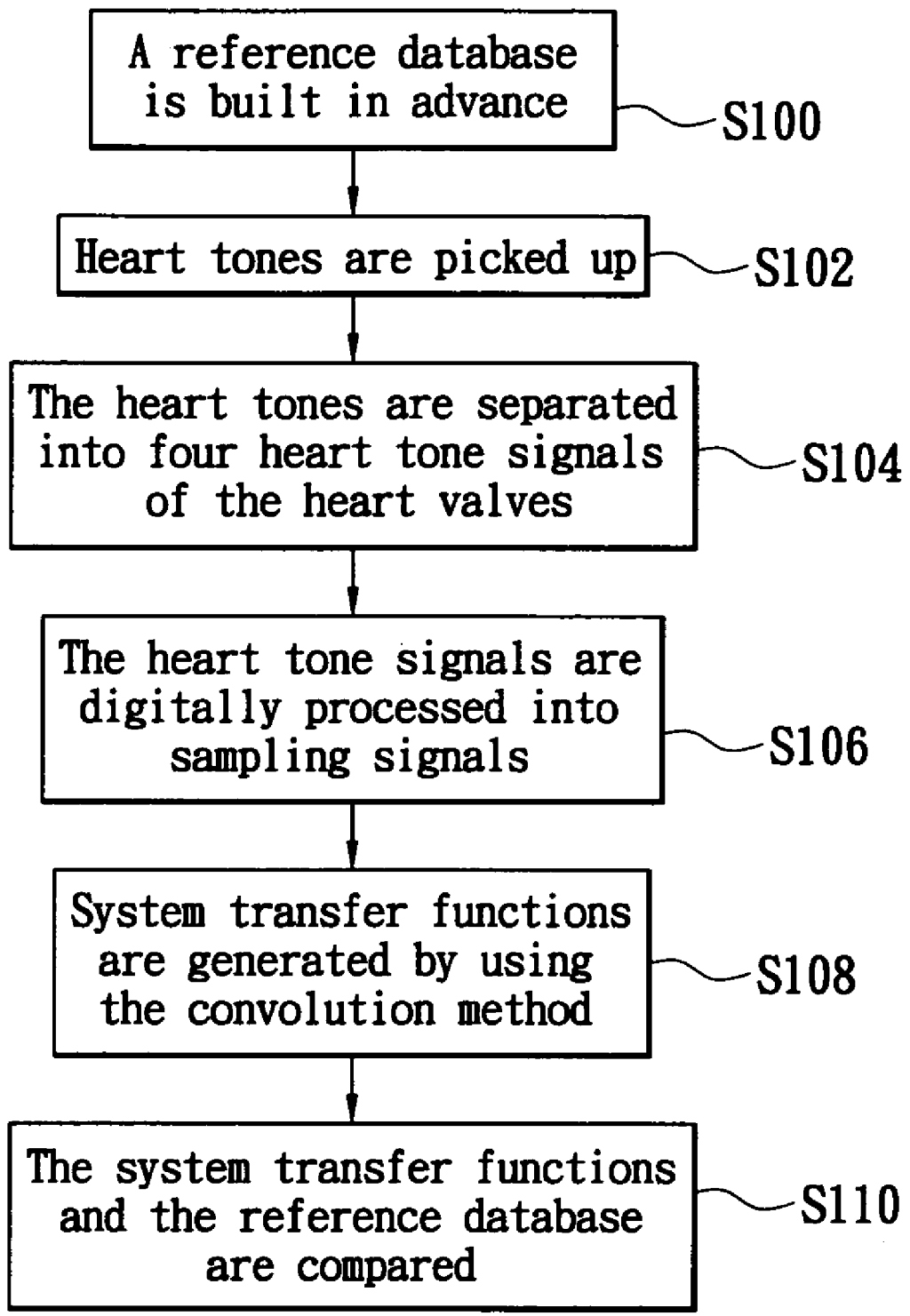
FIG. 1 is a flowchart of an automatic determination method of the damage of heart valves of the present invention.

As shown in FIG. 1, an automatic determination method of the damage of heart valves of the present invention comprises the following steps. First, a reference database is installed in advance (Step S100). The reference database stores relationship data between accumulated clinic damages of heart valves and heart tones. Three or more heart tone microphones are simultaneously used to pick up and record heart tones, or the heart tones are separately measured at the aortic valve, the pulmonary valve, the tricuspid valve and the mitral valve of the heart (Step S102). Next, the heart tones are separated into four heart tone signals of the aortic valve, the pulmonary valve, the tricuspid valve and the mitral valve of the heart based on the timing characteristics and related techniques (Step S104). In one embodiment of the present invention, the heart tone signals can be obtained by subtracting the heart tone measured at the pulmonary valve from the heart tone measured at the aortic valve, subtracting the heart tone measured at the aortic valve from the heart tone measured at the pulmonary valve, subtracting the heart tone measured at the tricuspid valve from the heart tone measured at the mitral valve, and subtracting the heart tone measured at the mitral valve from the heart tone measured at the tricuspid valve. The heart tone signals can also be obtained in other ways of operations.

Subsequently, these separated heart tone signals are digitally processed into sampling signals (Step S106). The convolution method is then used to process the sampling signals to produce system transfer functions (Step S108). These system transfer functions are calculated out by using the impulse responses. That is, an input impulse and the heart tone signals are convoluted to get the system transfer functions. Finally, the system transfer functions of the heart valves are separately compared with the built reference database to verify and determine the damage of the four heart valves (Step S110).

Figure 2:
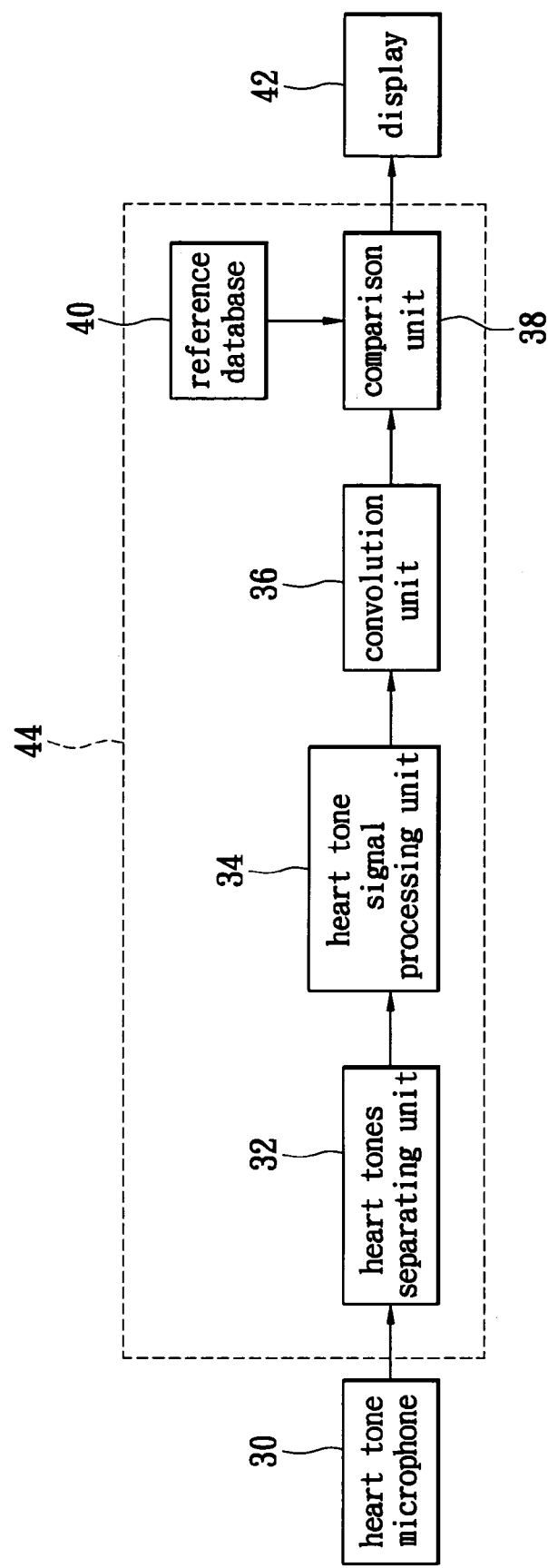
FIG. 2 is a block diagram of an automatic determination device of the damage of heart valves of the present invention.
Figure 3A:
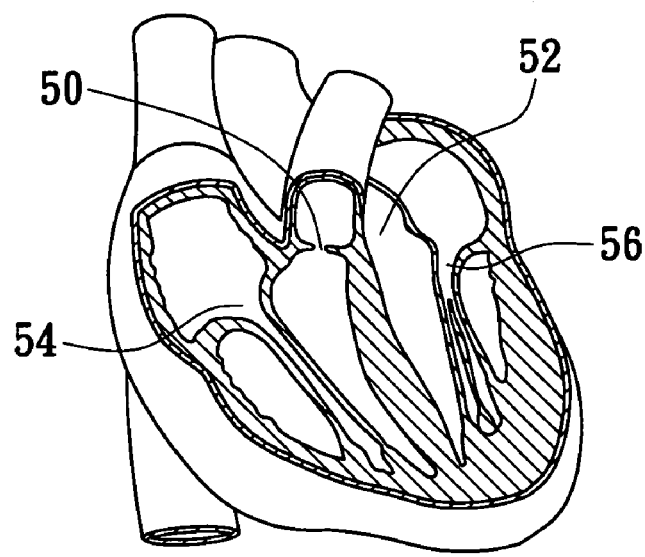
FIG. 3A is a diagram showing the positions of the aortic valve, the pulmonary valve, the tricuspid valve and the mitral valve of the heart system.
Figure 3B:
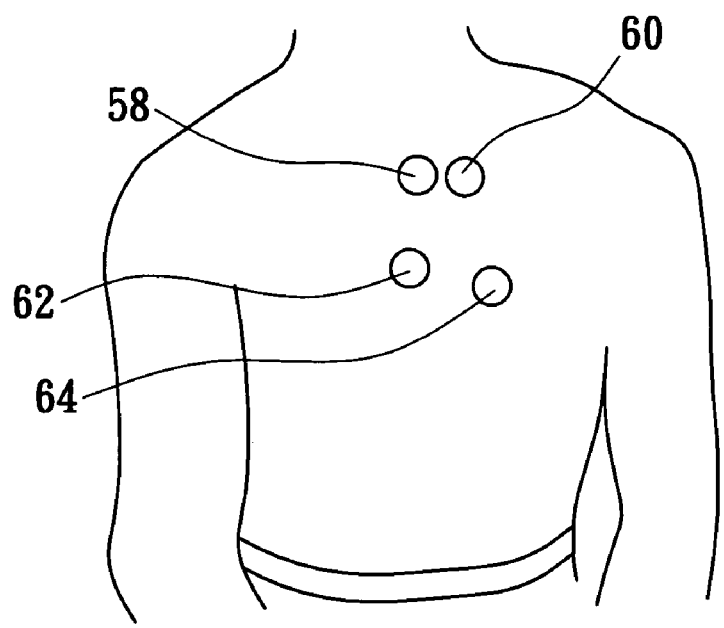
FIG. 3B is a diagram showing the measurement positions of heart tones in the present invention.

As shown in FIG. 2, an automatic determination device of the damage of heart valves of the present invention comprises a heart tone microphone 30 for separately recording heart tones or three or more heart tone microphones 30 for simultaneously recording the heart tones at the aortic valve, the pulmonary valve, the tricuspid valve and the mitral valve of the heart. FIG. 3A shows the positions of the aortic valve 52, the pulmonary valve 50, the tricuspid valve 54 and the mitral valve 56. FIG. 3B is a diagram showing the measurement positions of heart tones at the aortic valve 52, the pulmonary valve 50, the tricuspid valve 54 and the mitral valve 56.

The automatic determination device also comprises a signal processing system 44, which is connected with the heart tone microphones 30 and used for digital processing of the heart tones recorded by the three or more heart tone microphone and operation and comparison of system transfer functions. The system processing system 44 comprises a reference database 40 and a heart tones separating unit 32. The reference database 40 is used to store relationship data between accumulated clinical damage of heart valves and heart tones. The heart tones separating unit 32 is connected with the heart tone microphones and used to separate the heart tones recorded by the three or more heart tone microphones 30 into heart tone signals of the aortic valve, the pulmonary valve, the tricuspid valve and the mitral valve of the heart based on the timing characteristics and related techniques.

The heart tone signals of the heart valves can be obtained by subtracting the heart tone measured at the pulmonary valve from the heart tone measured at the aortic valve, subtracting the heart tone measured at the aortic valve from the heart tone measured at the pulmonary valve, subtracting the heart tone measured at the tricuspid valve from the heart tone measured at the mitral valve, and subtracting the heart tone measured at the mitral valve from the heart tone measured at the tricuspid valve. The heart tone signals can also be obtained in other ways of operations.

The automatic determination device of the damage of heart valves of the present invention further comprises a heart tone signal digital processing unit 34, a convolution unit 36, a comparison unit 38 and a display 42. The heart tone signal digital processing unit 34 is connected with the heart tones separating unit 32 and used to process the separated heart tone signals of the heart valves into sampling signals. The convolution unit 36 is connected with the heart tone signal digital processing unit 34 and used to process the sampling signals for producing system transfer function through the convolution method. The comparison unit 38 is connected with the convolution unit 36 and the reference database 40 and used to separately compare the system transfer functions of the four heart valves with the built reference database 40 to automatically determine the damages of the four heart valves. The display 42 is connected with the comparison unit 38 and used to display the damage of the heart valves.

Although the present invention has been described with reference to the preferred embodiment thereof, it will be understood that the invention is not limited to the details thereof. Various substitutions and modifications have been suggested in the foregoing description, and other will occur to those of ordinary skill in the art. Therefore, all such substitutions and modifications are intended to be embraced within the scope of the invention as defined in the appended claims.

We claim:

1. A device for automatically detecting heart valve damage, comprising:

at least one heart tone microphones for recording heart tones;

a signal processing system, connected with said at least one heart tone microphone, used for digital processing said heart tones recorded by said at least one heart tone microphone, and for operation and comparison of system transfer functions, wherein said signal processing system comprises:

a reference database for storing relationship data between accumulated clinical heart valve damage and accumulated heart tones;

a heart tones separating unit, connected with said at least one heart tone microphone, configured to separate said heart tones into four heart tone signals of the aortic valve, the pulmonary valve, the tricuspid valve and the mitral valve of the heart based on timing characteristics and related techniques;

a heart tone signal digital processing unit, connected with said heart tones separating unit, configured to process the separated heart tone signals into sampling signals;

a convolution unit, connected with said heart tone signal digital processing unit, configured to process said sampling signals for producing the system transfer functions through a convolution method; and a comparison unit, connected with said convolution unit and said reference database, configured to compare separately said system transfer functions of the four heart tone signals to detect heart valve damage to four heart valves; and a display connected with said signal processing system and used to display heart valve damage.

2. The device for automatically detecting heart valve damage as claimed in claim 1, wherein a number of said heart tone microphones is three or more.

3. The device for automatically detecting heart valve damage as claimed in claim 1, wherein said heart tones separating unit subtracts a heart tone measured at the pulmonary valve from a heart tone measured at the aortic valve, subtracts a heart tone measured at the aortic valve from a heart tone measured at the pulmonary valve, subtracts a heart tone measured at the tricuspid valve from a heart tone measured at the mitral valve, and subtracts a heart tone measured at the mitral valve from a heart tone measured at the tricuspid valve.

* * * * *